(12) United States Patent
Jamison

(10) Patent No.: US 8,333,587 B2
(45) Date of Patent: Dec. 18, 2012

(54) GRS IMPLANT DRILLING GUIDE

(76) Inventor: Mark K. Jamison, Beverly Hills, CA (US)

(*) Notice: Subject to any disclaimer, the term of this patent is extended or adjusted under 35 U.S.C. 154(b) by 893 days.

(21) Appl. No.: 12/152,859

(22) Filed: May 19, 2008

(65) Prior Publication Data

US 2009/0286197 A1 Nov. 19, 2009

(51) Int. Cl.
*A61C 3/00* (2006.01)
(52) U.S. Cl. .......................................................... 433/75
(58) Field of Classification Search ............... 433/72, 433/75, 76, 214; 434/263, 270; 623/11.1, 623/901; 606/96–98
See application file for complete search history.

(56) References Cited

U.S. PATENT DOCUMENTS

| | | | |
|---|---|---|---|
| 2002/0177104 A1* | 11/2002 | Klein et al. | 433/173 |
| 2004/0219478 A1* | 11/2004 | Harter | 433/75 |
| 2004/0219479 A1* | 11/2004 | Malin et al. | 433/75 |
| 2006/0188840 A1* | 8/2006 | Verban | 433/75 |
| 2006/0240379 A1* | 10/2006 | Weinstein | 433/76 |
| 2007/0077532 A1* | 4/2007 | Harter | 433/75 |
| 2010/0062389 A1* | 3/2010 | Drews et al. | 433/75 |

* cited by examiner

*Primary Examiner* — Todd E. Manahan
*Assistant Examiner* — Matthew Nelson
(74) *Attorney, Agent, or Firm* — Neil John Graham

(57) ABSTRACT

A template for drilling channels in a dental alveolar ridge to receive dental implants wherein interchangeable drilling guides are precisely located in a manner that each channel is formed with successive drills that are guided in the same predetermined location, axial inclination and penetration depth in the alveolar ridge.

19 Claims, 6 Drawing Sheets

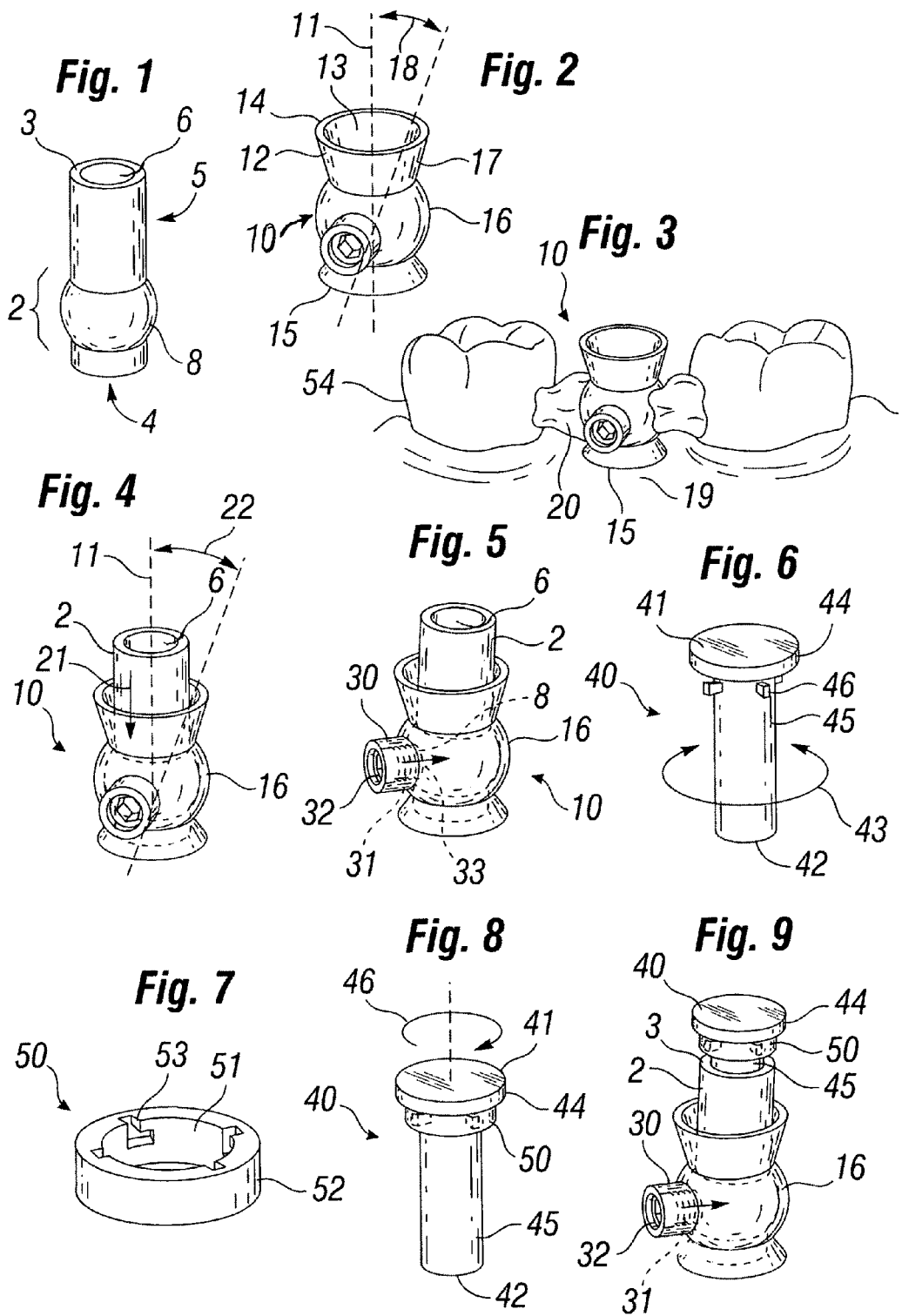

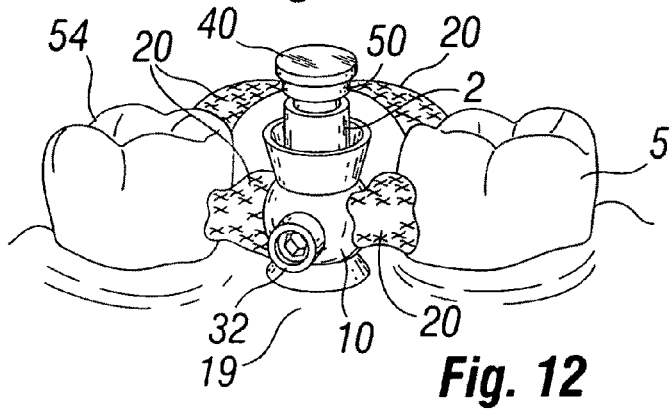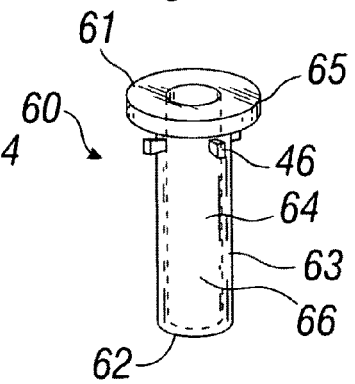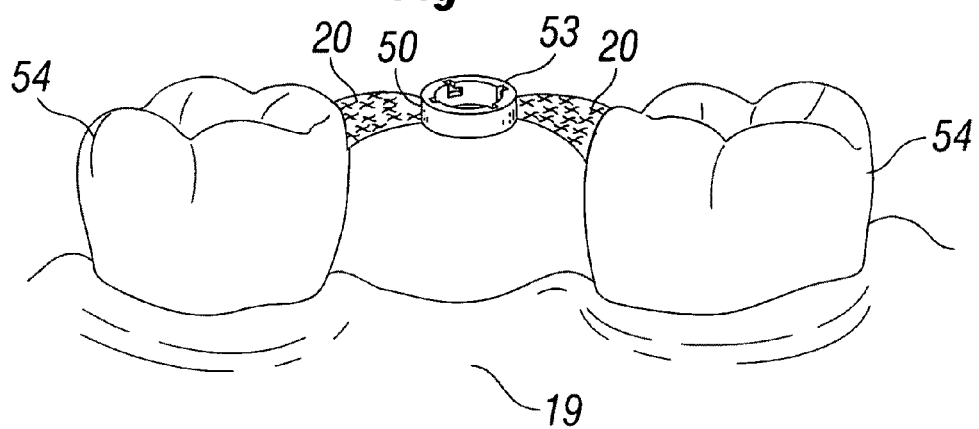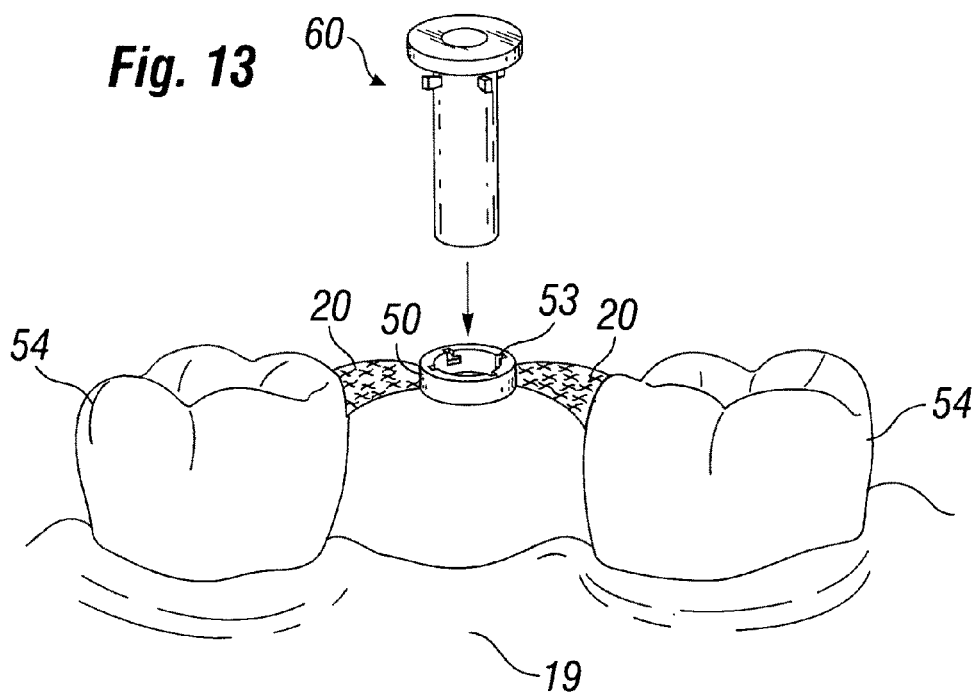

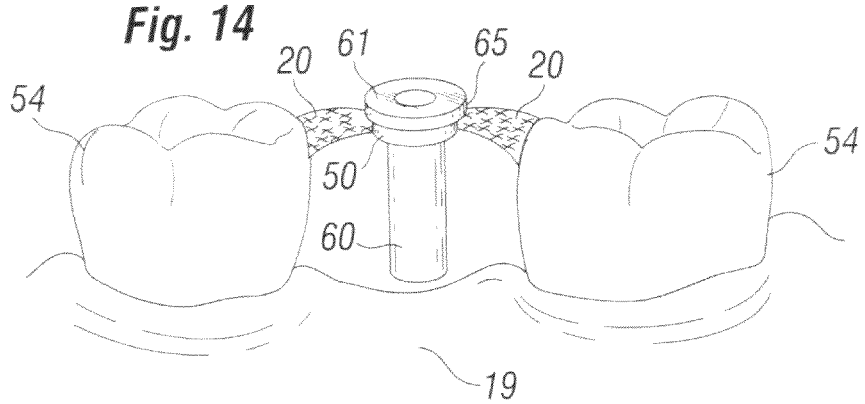
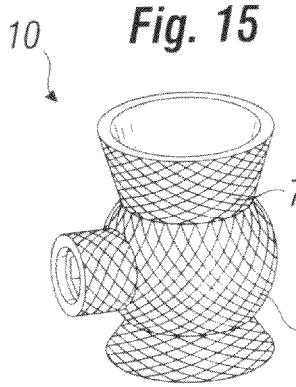
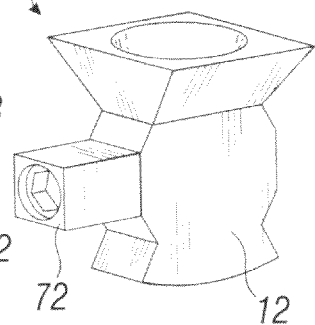
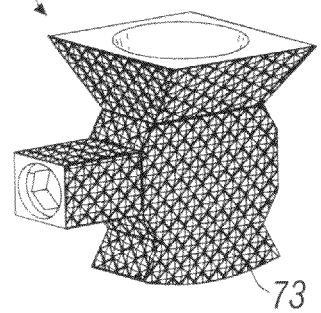
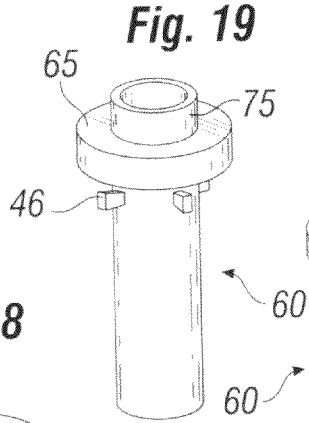
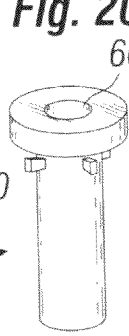
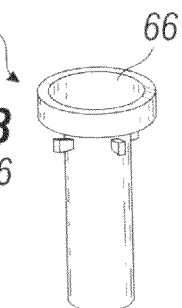
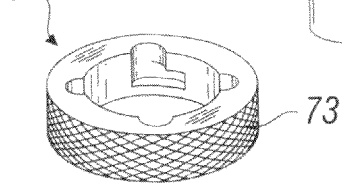

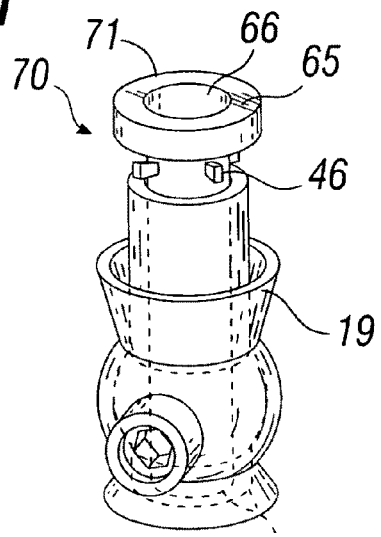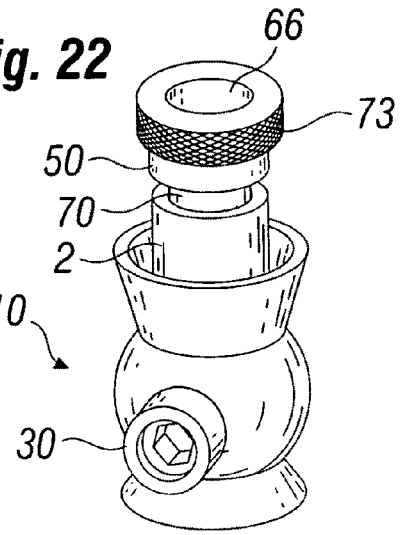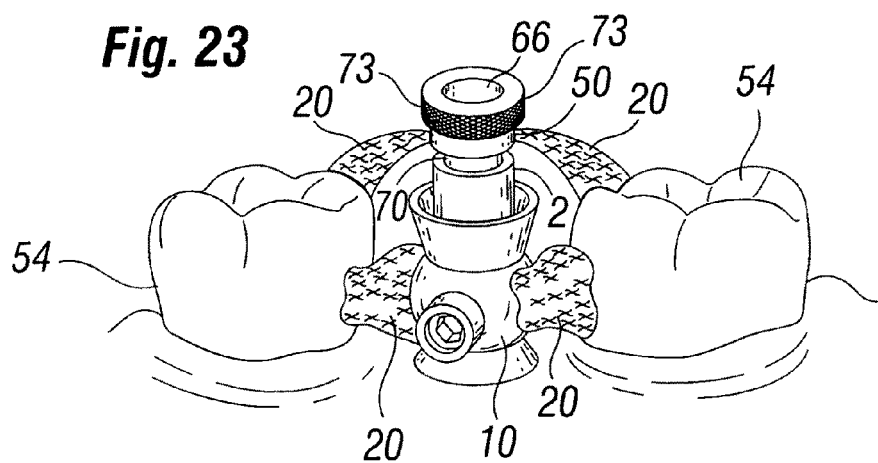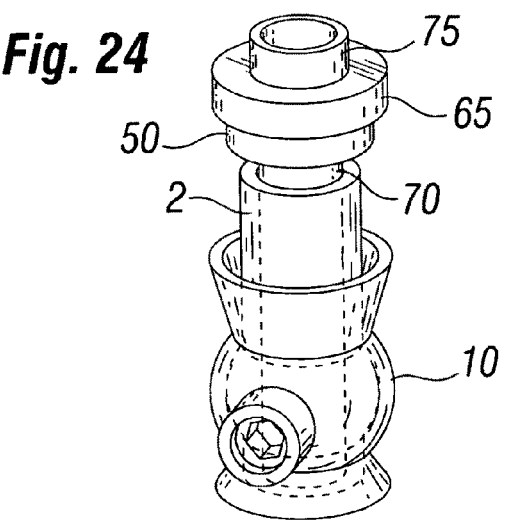

GRS IMPLANT DRILLING GUIDE

BACKGROUND OF THE INVENTION

1. Field of the Invention

The present invention relates generally to the field of dental implants, and more particularly to methods and devices for installing a dental implant in the correction position within a jaw.

2. Description of the Related Art

Implant dentistry involves the restoration of one or more teeth in a patient's mouth by the use of artificial implants to support prosthetic crowns. The process for replacing a missing tooth involves placing an implant, adding a post to receive a crown and adding a crown. The alveolar bone is first accessed through the patient's gum tissue. The specific site in the alveolar bone where the implant will be anchored is prepared by drilling and/or reaming to accommodate the width of the dental implant to be inserted. The dental implant is then inserted into the hole, typically by screwing the implant in, although other techniques are known for introducing the implant in the jawbone. A temporary healing cap is secured over the exposed proximal end in order to seal an internal bore of the implant. The patient's gums are then sutured over the implant to allow the implant site to heal and to allow desired osseointegration to occur. Complete osseointegration typically takes anywhere from three to ten months. In the alternative, the cap is placed immediately. The restoration is completed by placing a post to the implant and placing a cap over the post.

It is important that the implant is installed at a proper or optimum position and angle with respect to the particular structure of the alveolar bone that is receiving the implant. The implant must be installed within the alveolar bone in order to insure the required support and longevity of the implant. The implant must also be positioned optimally in order to place a functional and esthetic cap or prosthesis. Many techniques and devices have been developed and used for the correct placement of a dental implant. Many such techniques tend to depend on the skill and experience of the oral surgeon.

SUMMARY OF THE INVENTION

The purpose of the invention is to provide all dentists and specialists alike with an accurate and reliable process in which to surgically place dental implants. Additionally, lab technicians will also be able to use the process. They will be able to create surgical stents for implant procedures coupled by the significant benefit of being able to communicate with the dentist/specialist regarding the functional results of a restoration prior to implant placement. There remains a general need for an improved device and method for determining the proper or optimum position, angle and depth of a dental implant with respect to the structure of the alveolar bone. Successive dental drills, each with increasing size, are used to drill a channel within alveolar bone in which to receive the dental implant.

A mold is made of the patient's mouth. A dental model is made from the mold and upon that dental model the entry position of the future implant is determined. This is the first step. A bondable thermoplastic-vacuum-formed material is then formed over the dental model. The GRS implant drilling guide is then placed and secured with putty upright over the chosen entry position of the dental implant. The GRS implant drilling guide is essentially a hollow vertical housing containing a vertical hollow cylinder, the vertical hollow cylinder having the ability to be moved 20 degrees in all directions and locked into place with a locking set screw. In a preferred embodiment a vertical positioning guide with an attached surgical circular ring is placed within the interior of the hollow cylinder and is moved until the correct angle of the future implant channel is determined. At this point the set screw is turned clockwise, locking the vertical hollow cylinder, containing the positioning guide and surgical circular ring, into position. The positioned surgical circular ring is the structure of most importance because it is secured to the adjacent bondable vacuum-formed thermoplastic plate with putty and the cylinder and housing with the set screw housing are removed. The surgical stent is ready for transfer to the mouth. The surgical circular ring is attached over the dental ridge and the first surgical sleeve is placed into the surgical circular ring and locked in place by turning it clockwise. The first surgical sleeve would have a small internal diameter to receive a small diameter dental drill. A series of progressively larger diameter dental drills, each with a matching size surgical sleeve, are the used. The first surgical sleeve is turned counterclockwise and removed and each succeeding surgical guide is placed using the preceding steps. The depth of the dental drill penetration is controlled by a selection of spacers at the top of the surgical sleeve at the entry point of the dental drill. Each size dental drill enters the jaw at the same position and angle and drills to the same depth.

In another preferred embodiment the positioning guide is eliminated and a drilling guide with an external diameter the same as the positioning guide is used. Preferably this drilling guide would have the starting internal diameter to match the first dental drill to be used. In another embodiment the surgical circular ring is held in position with a thermo-vacuum-formed plate.

The above embodiments describe a single tooth; but the technique lends itself to multiple implants done at the same time. The GRS implant drilling guide may be used without opening a flap in the gum tissue of the patient

BRIEF DESCRIPTION OF THE DRAWINGS

FIG. 1 is a perspective view of a cylinder;

FIG. 2 is a perspective view of a housing;

FIG. 3 is a perspective view the housing mounted between two teeth;

FIG. 4 is a perspective view of the cylinder inside the housing;

FIG. 5 is a perspective view of FIG. 4 with a locking set screw;

FIG. 6 is a perspective view of a positioning guide;

FIG. 7 is a perspective view of a surgical ring;

FIG. 8 is a perspective view of a the positioning guide inserted within the surgical ring;

FIG. 9 is a perspective view of a of FIG. 8 inserted inside the housing;

FIG. 10 is a perspective view of a FIG. 8 inserted between two teeth;

FIG. 11 is a perspective view of a longitudinal sleeve;

FIG. 12 is a perspective view of a surgical circular ring mounted between two teeth;

FIG. 13 is a perspective view of a longitudinal sleeve being placed in FIG. 12;

FIG. 14 is a perspective view of a longitudinal sleeve placed in the mounted surgical ring;

FIG. 15 is a perspective view of a housing with an irregular surface;

FIG. 16 is a perspective view of a housing with a rectangular exterior;

FIG. 17 is a perspective view of FIG. 16 with an irregular exterior;

FIG. 18 is a perspective view of FIG. 7 with an irregular exterior;

FIG. 19 is a perspective view of FIG. 11 with a spacer;

FIG. 20 is perspective views of multiple longitudinal sleeves with varying internal diameters;

FIG. 21 is a perspective view of a combination surgical sleeve fitted within a cylinder/housing;

FIG. 22 is a perspective view of a FIG. 21 with a surgical ring;

FIG. 23 is a perspective view of FIG. 22 mounted between two teeth;

FIG. 24 is a perspective view of FIG. 22 with a spacer;

DETAILED DESCRIPTION OF THE INVENTION

Figure 25:
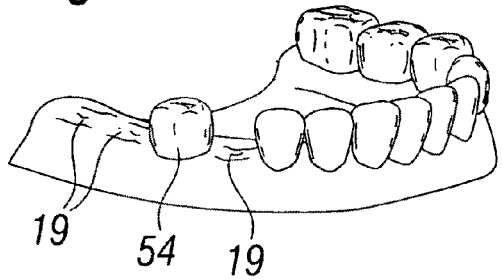
FIG. 25 is a perspective view of a model of teeth.

FIG. 1 discloses a cylinder 2 with a long axis comprising an open top first end 3 and an open lower second end 4, an exterior circular circumference 5 and a circular hollow interior 6, the circular hollow interior 6 extending from the open top first end 3 to the open lower second end 4 wherein the external circular circumference 5 adjacent to the second end 4 has a circular circumferential ball-shaped enlargement 8. FIG. 2 discloses a housing 10 with a long axis 11 comprising an exterior 12 and a hollow interior 13 with a circular circumference, an open top first end 14 and an open lower second end 15, the hollow interior 13 extending from the open top first end 14 to the open lower second end 15, a circular ball-shaped enlargement 16 of the interior circumference adjacent to the lower second end 15 is shaped to receive the circumferential circular ball-shaped enlargement 8 of the cylinder 2, the hollow interior 13 progressively enlarges 17 from the circular ball-shaped enlargement 16 towards the top first end 14, the progressive enlargement 17 at 20 degrees 18 to the long axis 11.

FIG. 3 shows the housing 10 second end 15 secured to a dental edentulous ridge 19 and adjacent teeth 54 with a putty 20. In FIG. 4 the cylinder 2 is fitted within the housing 10. The circular circumferential ball-shaped enlargement 8 of the cylinder 2 fits within the circular ball-shaped enlargement 16 of the housing 10 and the first end 3 of the cylinder 2 fits within the top first end 14 of the housing 10 wherein the cylinder 2 may be pivoted 22 around the ball shaped enlargement 8 end 4 up to 20 degrees from the housing long axis 11. Referring to FIG. 5, a threaded set screw housing 30 containing a threaded channel 31 with a set screw 32 at a right angle to the housing 10 long axis 11 adjacent to the circumferential circular ball-shaped enlargement 16, the threaded channel 31 opening into the housing interior 13 wherein when the set screw 32 is screwed inwards the set screw 32 is seated against 33 the circular circumferential ball-shaped enlargement 8 of the cylinder 2 locking the cylinder 2 in its axial position 34 within the housing 10.

FIG. 6 discloses a longitudinal positioning guide 40 with a first 41 and second end 42 and an axial circumference 43 comprised of a platform 44 at the first end 41, a longitudinal stem 45 extending from the platform 44 to the second end 42 and circumferential male keyways 46 on the longitudinal stem 45 adjacent to the platform 44. FIG. 7 discloses a surgical circular ring 50 with an interior 51 and an exterior 52, the interior 51 containing keyway grooves 53 which engage the male keyways 46 of the positioning guide 40 when the stem 45 of the positioning guide 40 is placed, as in FIG. 8, within the interior 51 of the circular surgical ring 50 and turned clockwise wherein, with the surgical circular ring 50 attached to the positioning guide 40, the second end 42 of the positioning guide 40 is placed, as in FIG. 9, in the first end 3 of the cylinder 2 and seated to the second end 4 of the cylinder 2 where the positioning guide 40 is used to position the cylinder 2.

FIG. 9 discloses a preferred embodiment of the GRS implant drilling guide. In FIG. 10, when the cylinder 2 is correctly positioned the set screw 32 is turned clockwise, which locks the cylinder 2 in position, the surgical circular ring 50 is then secured to the edentulous ridge 19 and adjacent teeth 54 with a putty 20. The cylinder 2, housing 10, with set screw housing 30 and longitudinal positioning guide 40, are removed. FIG. 11 discloses a longitudinal surgical sleeve 60 with a first end 61, second end 62, an exterior 63 and an interior 64 wherein the first end 61 has a platform 65, adjacent to the platform 65 the exterior 63 of the surgical sleeve 60 contains circumferential male keyways 46, the interior 64 defines a longitudinal tube 66 sized to receive a drill. The positioning guide 40 has been removed, FIG. 12, from the circular surgical ring 50. The second end 62 of the surgical sleeve 60 is placed, FIG. 13, within the surgical circular ring 50 seated and is turned clockwise, FIG. 14, wherein the male keyways 46 of the surgical sleeve 60 engage the keyway grooves 53 of the surgical circular ring 50. The surgical sleeve 60 is now positioned in the same position as the positioning guide 40 occupied and functions as a drilling guide. Successive sleeves with different size interior longitudinal tubes may be placed in exactly the same position relative to the edentulous dental ridge 19. FIG. 15 discloses a housing 10 exterior 12 which is round. FIG. 15 also shows a housing 10 exterior 12 with an irregular surface 73 in order to enhance the adhesion of the putty 20 to housing exterior 12. In FIG. 16 the housing exterior 12 is rectangular 72. FIG. 17 shows the rectangular 72 housing exterior with an irregular surface 73 in order to enhance the adhesion of the putty 20 to the housing 10 exterior 12.

In FIG. 18 a surgical circular ring 50 has a surface; the surface is irregular 73 in order to enhance the adhesion of the putty 20 to the surgical circular ring 50 exterior 52. FIG. 19 shows the surgical sleeve 60 platform 65 with an outside surface facing away from the sleeve platform 65. Various thicknesses of spacers 75 are placed on the outside surface controlling the depth a dental pilot drill penetrates a dental edentulous ridge 19, FIG. 10. a thicker spacer 75 results in less penetration. FIG. 20 shows multiple longitudinal surgical sleeves 60, each having an interior longitudinal tube 66, each interior tube 66 with an increasingly larger diameter sized to fit increasingly larger diameter dental pilot drills.

Putties 20, for securing the surgical circular ring 50, depicted in FIGS. 3, 10, 12, 13 and 14, are dental materials such as: sticky wax, light cure putty, such as Triad, acrylics such as Jet used for denture repair and temporary filling materials.

In another preferred embodiment, FIG. 21, the GRS implant drilling guide is comprised of the same cylinder 2 housing 10 and threaded set screw housing 30 as disclosed in FIGS. 1, 2, 3, 4 and 5. FIG. 21 wherein FIG. 21 discloses a combination longitudinal positioning guide and surgical sleeve 70 with a first end 71, second end 71, an exterior 73 and an interior 66 wherein the first end 71 has a platform 74, adjacent to the platform 74 the exterior 73 of the sleeve contains circumferential male keyways 46, the interior 66 defines a surgical sleeve 66 sized to receive a pilot drill. FIGS. 7 and 22 disclose a circular surgical circular surgical ring 56 with an interior 51 and an exterior 52, the interior 51 containing keyway grooves 53 which engage the male keyways 46 of the combination longitudinal positioning guide and surgical sleeve 70, FIG. 21, when the combination longitudinal positioning guide and surgical sleeve 70 second end 72 is placed within the interior of the surgical circular surgical ring 56 and turned clockwise wherein, with the surgical circular surgical ring attached to the combination longitudinal positioning guide and surgical sleeve 70, the second end of the positioning guide is placed in the first end of the cylinder 2 and seated to the second end of the cylinder where the combination longitudinal positioning guide and surgical sleeve 70 is used to position the cylinder 2, when the cylinder 2 is correctly positioned the set screw 32, FIGS. 5 and 22 is turned clockwise which locks the cylinder 2 in position. In FIG. 23 the surgical circular ring 50 is then secured to the edentulous ridge 19, FIG. 14, and adjacent teeth 54 with a putty 20 and the cylinder 2 within the housing 10 with the set screw housing 30 may remain or be removed. In FIG. 24 the combination longitudinal positioning guide and surgical sleeve 70 platform 74 has an outside surface facing away from the sleeve wherein various thicknesses of spacers 75 are placed on the outside surface controlling the depth a dental pilot drill penetrates a dental edentulous ridge 19. A thicker spacer 75 results in less penetration.

Figure 26:
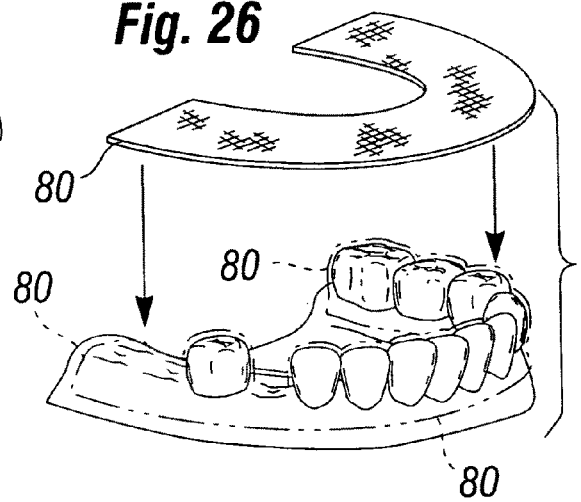
FIG. 26 is a perspective view of thermo-vacuum-formed material being placed on the model.
Figure 27:
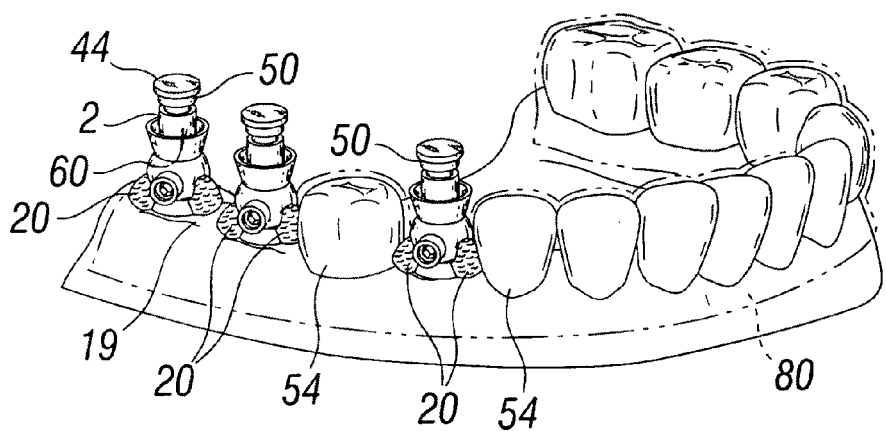
FIG. 27 is a perspective view of FIG. 9 placed over the alveolar ridge.
Figure 28:
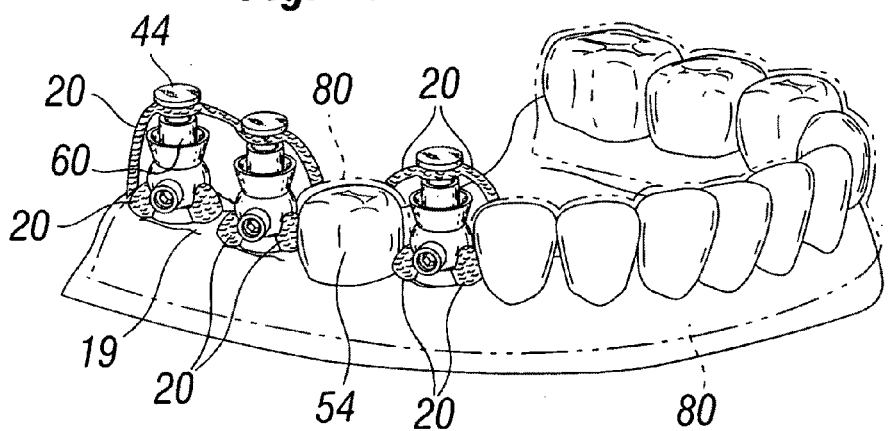
FIG. 28 is a perspective view of a FIG. 27 with the surgical rings attached.
Figure 29:
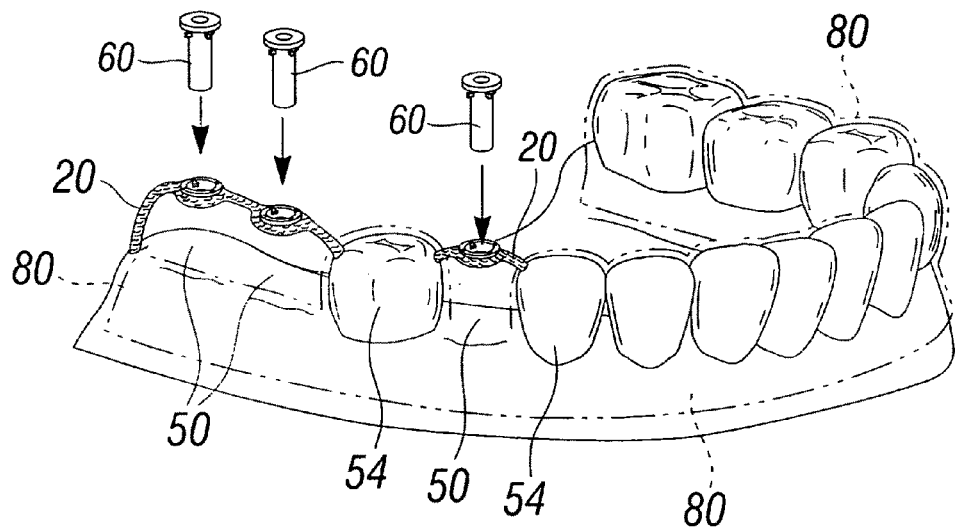
FIG. 29 is a perspective view of FIG. 27 with only the surgical rings remaining.
Figure 30:
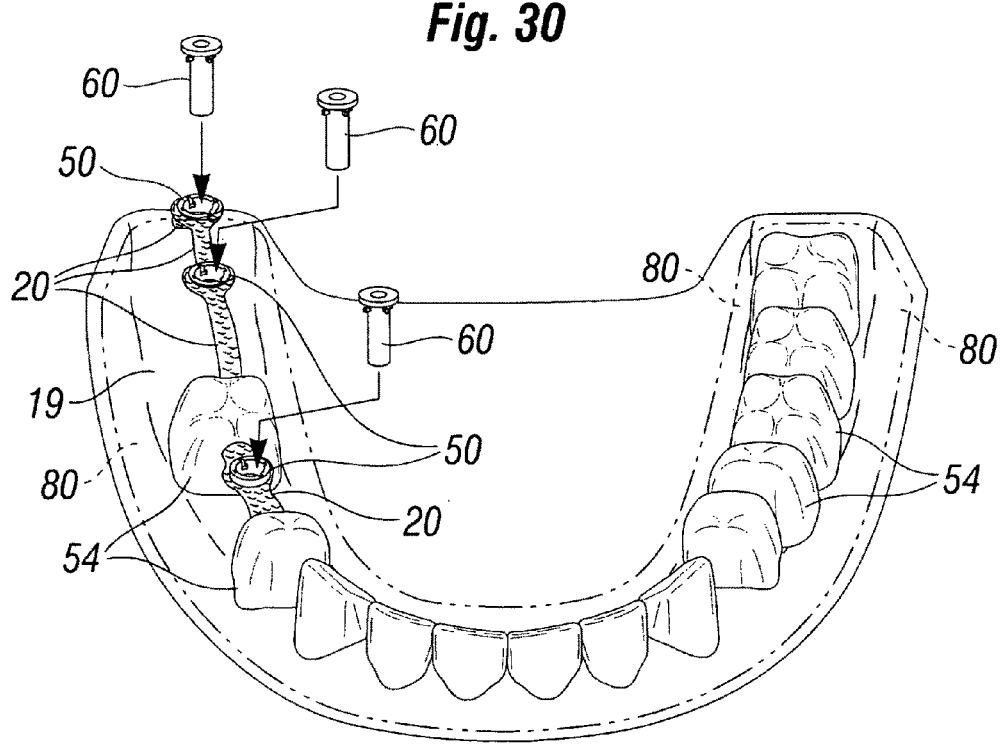
FIG. 30 is a perspective view of the vacuum-formed plate with attached surgical rings in the mouth.

FIG. 25 discloses a dental model with an alveolar ridge 19 and teeth 54. In FIG. 26 there is a thermo-vacuum-forming plate 80 which is vacuum-formed over the dental model. The thermo-vacuum-forming plate 80 ideally is a material that adhesives will adhere to, such as polycarbonate. In FIG. 27 the longitudinal sleeves 60 are placed on the alveolar ridge 19 in the positions the implant holes are to be drilled. The longitudinal sleeves 60 are attached to the thermo-vacuum-forming plate 80 with putty 20 that is removable. Dental sticky wax is an example. At this point each cylinder 2 is angled into the correct position to guide the drills in the process of forming the implant shaft. The locking pins are tightened to secure the chosen cylinder 2 positions. FIG. 28 has the surgical circular rings 50 separately secured to the adjacent thermo-vacuum-forming plate 80. In an alternative embodiment the surgical circular rings 50 may be secured with a thermo-vacuum-forming plate 80. FIG. 29 discloses the longitudinal sleeves 60 removed and the housings 10 removed leaving the surgical circular rings 50 suspended over the alveolar ridge 19. The thermo-vacuum-forming plate 80 with the mounted surgical circular rings 50 is removed from the dental model and holes are drilled in the thermo-vacuum-forming plate 80 underneath each circular surgical ring 50. The holes allow for the dental drill to have access to the alveolar ridge 19. FIG. 30 shows thermo-vacuum-forming plate 80 with the mounted surgical circular rings 50 placed in the mouth with the longitudinal sleeves 80 ready to be placed into the mounted surgical circular rings 50. Each surgical circular ring 50 receives successively larger sleeves to accommodate each larger diameter drill.

What is claimed:

1. A GRS implant drilling guide for placing a pilot hole for a dental implant post comprising:

a cylinder with a long axis comprising an open top first end, an open lower second end, an exterior circular circumference and a circular hollow interior, the circular hollow interior extending from the open top first end to the open lower second end wherein the external circular circumference adjacent to the second end has a circular circumferential ball-shaped enlargement;

a housing with a long axis comprising an exterior and a hollow interior with a circular circumference, an open top first end and an open lower second end, the hollow interior extending from the open top first end to the open lower second end, a circular ball-shaped enlargement of the interior circumference adjacent to the lower second end shaped to receive the circumferential circular ball-shaped enlargement of the cylinder, the hollow interior progressively enlarges from the circular ball-shaped enlargement towards the top first end, the progressive enlargement at 20 degrees to the long axis of the housing wherein in use the second housing end is placed upon an edentulous dental ridge where it is secured, or held in place, with a putty and the circular circumferential ball-shaped enlargement of the cylinder fits within the circular ball-shaped enlargement of the housing and the first end of the cylinder fits within the top first end of the housing wherein the cylinder may be pivoted around the ball shaped enlargement end up to 20 degrees from the housing long axis;

a threaded set screw housing containing a threaded channel with a set screw at a right angle to the housing long axis adjacent to the circumferential circular ball-shaped enlargement, the threaded channel opening into the housing interior wherein when the set screw is turned clockwise inwards until the set screw is seated against the circular circumferential ball-shaped enlargement of the housing, locking the cylinder in its axial position within the housing;

a longitudinal positioning guide with a first and second end and an axial circumference comprised of a platform at the first end, a longitudinal stem extending from the platform to the second end and circumferential male keyways on the stem adjacent to the platform;

a surgical circular ring with an interior and an exterior, the interior containing keyway grooves which engage the male keyways of the positioning guide when the stem of the positioning guide is placed within the interior of the surgical circular ring and turned clockwise wherein, with the surgical circular ring attached to the positioning guide, the second end of the positioning guide is placed in the first end of the cylinder and seated to the second end of the cylinder where the positioning guide is used to position the cylinder, when the cylinder is correctly positioned the set screw is turned clockwise which locks the cylinder in position, the surgical circular ring is then secured to the edentulous ridge and adjacent teeth with a putty and the cylinder, housing with set screw housing and longitudinal positioning guide are removed; and a longitudinal surgical sleeve with a first end, second end, an exterior and an interior wherein the first end has a platform, adjacent to the platform the exterior of the sleeve and contains circumferential male keyways, the interior defines a longitudinal tube sized to receive a drill, the positioning guide is removed from the surgical circular ring and second end of the surgical sleeve is placed within the surgical circular ring, seated and is turned clockwise wherein the male keyways of the surgical sleeve engage the keyway grooves of the surgical ring, the surgical sleeve is now positioned in the same position as the positioning guide occupied and functions as a drilling guide, successive sleeves with different size interior longitudinal tubes may be placed in exactly the same position relative to the edentulous dental ridge.

2. A GRS implant drilling guide as in claim 1 wherein the housing exterior is round.

3. A GRS implant drilling guide as in claim 2 wherein the housing exterior has a surface, the surface is irregular in order to enhance the adhesion of the putty to housing exterior.

4. A GRS implant drilling guide as in claim 1 wherein the housing exterior is rectangular.

5. A GRS implant drilling guide as in claim 4 wherein the housing exterior has a surface, the surface is irregular in order to enhance the adhesion of the putty to housing exterior.

6. A GRS implant drilling guide as in claim 1 wherein the circular surgical circular ring has a surface, the surface is irregular in order to enhance the adhesion of the putty to surgical circular ring exterior.

7. A GRS implant drilling guide as in claim 1 wherein the surgical sleeve has a platform with an outside surface facing away from the sleeve and also comprises various thicknesses of spacers which are placed on the outside surface controlling the depth a dental pilot drill penetrates a dental edentulous ridge, a thicker spacer results in less penetration.

8. A GRS implant drilling guide as in claim 1 wherein multiple longitudinal surgical sleeves each have an interior longitudinal tube, each interior tube with an increasingly larger diameter sized to fit increasingly larger diameter dental pilot drills.

9. A GRS implant drilling guide as in claim 1 wherein the putties for securing the surgical circular ring and the housing in place are sticky wax, light cure acrylic and self-cure acrylic.

10. A GRS implant drilling guide for placing a pilot hole for a dental implant post comprising:
a cylinder with a long axis comprising an open top first end, an open lower second end, an exterior circular circumference and a circular hollow interior, the circular hollow interior extending from the open top first end to the open lower second end wherein the external circular circumference adjacent to the second end has a circular circumferential ball-shaped enlargement;
a housing with a long axis comprising an exterior and a hollow interior with a circular circumference, an open top first end and an open lower second end, the hollow interior extending from the open top first end to the open lower second end, a circular ball-shaped enlargement of the interior circumference adjacent to the lower second end shaped to receive the circumferential circular ball-shaped enlargement of the cylinder, the hollow interior progressively enlarges from the circular ball-shaped enlargement towards the top first end, the progressive enlargement at 20 degrees to the long axis of the housing wherein in use the second housing end is placed upon an edentulous dental ridge where it is secured with a putty, or held in place, and the circular circumferential ball-shaped enlargement of the cylinder fits within the circular ball-shaped enlargement of the of the housing and the first end of the cylinder fits within the top first end of the housing wherein the cylinder may be pivoted around the ball shaped enlargement end up to 20 degrees from the housing long axis;
a threaded set screw housing containing a threaded channel with a set screw at a right angle to the housing long axis adjacent to the circumferential circular ball-shaped enlargement, the threaded channel opening into the housing interior wherein when the set screw is turned clockwise inwards until the set screw is seated against the circular circumferential ball-shaped enlargement of the housing, locking the cylinder in its axial position within the housing;
a combination longitudinal positioning guide and surgical sleeve with a first end, second end, an exterior sized to fit within the cylinder and an interior wherein the first end has a platform, adjacent to the platform the exterior of the sleeve contains circumferential male keyways, the interior defines a surgical sleeve sized to receive a pilot drill; and
a surgical circular ring with an interior and an exterior, the interior containing keyway grooves which engage the male keyways of the combination longitudinal positioning guide and surgical sleeve when the stem of the positioning guide is placed within the interior of the surgical circular ring and turned clockwise wherein, with the surgical circular ring attached to the combination longitudinal positioning guide and surgical sleeve, the second end of the positioning guide is placed in the first end of the cylinder and seated to the second end of the cylinder where the combination longitudinal positioning guide and surgical sleeve is used to position the cylinder, when the cylinder is correctly positioned the set screw is turned clockwise which locks the cylinder in position, the surgical circular ring is then secured to the edentulous ridge and adjacent teeth with a putty and the cylinder, the housing with the set screw housing may remain or be removed.

11. A GRS implant drilling guide as in claim 10 wherein the housing exterior is round.

12. A GRS implant drilling guide as in claim 11 wherein the housing exterior has a surface, the surface is irregular in order to enhance the adhesion of the putty to housing exterior.

13. A GRS implant drilling guide as in claim 10 wherein the housing exterior is rectangular.

14. A GRS implant drilling guide as in claim 13 wherein the housing exterior has a surface, the surface is irregular in order to enhance the adhesion of the putty to housing exterior.

15. A GRS implant drilling guide as in claim 10 wherein the surgical circular ring has a surface, the surface is irregular in order to enhance the adhesion of the putty to surgical circular ring exterior.

16. A GRS implant drilling guide as in claim 10 wherein the surgical sleeve has a platform with an outside surface facing away from the sleeve and also comprises various thicknesses of spacers which are placed on the outside surface controlling the depth a dental pilot drill penetrates a dental edentulous ridge, a thicker spacer results in less penetration.

17. A GRS implant drilling guide as in claim 10 wherein combination longitudinal positioning guide and surgical sleeves have interior longitudinal tubes, each interior tube with an increasingly larger diameter sized to fit increasingly larger diameter dental pilot drills.

18. A GRS implant drilling guide as in claim 10 wherein the putties for securing the surgical circular ring and the housing in place are sticky wax, light cured, acrylic and self-cure acrylic.

19. A GRS implant drilling guide as in claim 10 wherein the combination longitudinal positioning guide and surgical sleeve is held in the surgical ring with a locking means such as springs.

* * * * *

UNITED STATES PATENT AND TRADEMARK OFFICE
CERTIFICATE OF CORRECTION

PATENT NO. : 8,333,587 B2  
APPLICATION NO. : 12/152859  
DATED : December 18, 2012  
INVENTOR(S) : Jamison Page 1 of 1

It is certified that error appears in the above-identified patent and that said Letters Patent is hereby corrected as shown below:

Please delete item "(76)" and insert item -- (76) Mark B. Jamison, Beverly Hills, CA --

Signed and Sealed this  
Twelfth Day of February, 2013

Teresa Stanek Rea  
*Acting Director of the United States Patent and Trademark Office*